United States Patent [19]

Yamada et al.

[11] 4,094,741
[45] June 13, 1978

[54] PROCESS FOR PREPARING D-(−)-N-CARBAMOYL-2-(PHENYL OR SUBSTITUTED PHENYL)GLYCINES

[75] Inventors: Hideaki Yamada, Kyoto; Satomi Takahashi, Takatsuki; Koji Yoneda, Amagasaki, all of Japan

[73] Assignee: Kanegafuchi Kagaku Kogyo Kabushiki Kaisha, Osaka, Japan

[21] Appl. No.: 764,635

[22] Filed: Feb. 1, 1977

[30] Foreign Application Priority Data

Feb. 4, 1976 Japan .................................. 51-11575
Dec. 3, 1976 Japan ................................. 51-145748

[51] Int. Cl.$^2$ ............................................ C12D 13/06
[52] U.S. Cl. ................................... 195/29; 195/51 R
[58] Field of Search ............................ 195/51 R, 29

[56] References Cited

U.S. PATENT DOCUMENTS

| 3,320,135 | 5/1967 | Okumura et al. ............ 195/29 |
| 3,964,970 | 6/1976 | Dinelli et al. ............... 195/29 |

*Primary Examiner*—Alvin E. Taneholtz
*Attorney, Agent, or Firm*—Armstrong, Nikaido, Marmelstein & Kubovcik

[57] ABSTRACT

A process for preparing D-(−)-N-carbamoyl-2-(phenyl or substituted phenyl)glycines by subjecting 5-(phenyl or substituted phenyl)hydantoins to the action of a cultured broth, cells or treated cells of microorganisms having a capability in asymmetrically hydrolyzing the hydantoin ring. D-(−)-N-carbamoyl-2-(phenyl or substituted phenyl)glycines are useful intermediates of medicines and can be readily converted to D-(−)-2-(phenyl or substituted phenyl) glycines known as available intermediates of antibiotics.

13 Claims, No Drawings

PROCESS FOR PREPARING D-(−)-N-CARBAMOYL-2-(PHENYL OR SUBSTITUTED PHENYL)GLYCINES

BACKGROUND OF THE INVENTION

The present invention relates to a novel process for preparing D-(−)-N-carbamoyl-2-(phenyl or substituted phenyl)glycines, and more particularly to a process for preparing D-(−)-N-carbamoyl-2-(phenyl or substituted phenyl)glycines by biochemically hydrolyzing 5-(phenyl or substituted phenyl)hydantoins by employing a cultured broth, cells or treated cells of microorganisms.

It is well known that D-(phenyl or substituted phenyl)glycines are available intermediates of antibiotics such as semi-synthetic penicillins and semi-synthetic cephalosporins. These intermediates are generally prepared by resolving the DL-forms, which are obtained by chemical syntheses, by means of a chemical or biochemical method. For instance, as a process for preparing such intermediates by the biochemical method of resolution, there are known a process for preparing D-phenylglycine comprising asymmetrically hydrolyzing DL-N-chloroacetylphenylglycine by employing acylase and a process for preparing D-4-methoxyphenylglycine comprising asymmetrically hydrolyzing DL-N-acyl-(4-methoxyphenyl)glycine by employing aminoacylase. These processes require the use of the expensive acylase enzyme and also require a step of racemization and a step of recovering a residual optical isomer.

SUMMARY OF THE INVENTION

The present invention provides a process for economically preparing intermediates of medicines, D-(−)-N-carbamoyl-2-(phenyl or substituted phenyl)glycines which can be readily converted to D-(−)-2-(phenyl or substituted phenyl)glycines known as available intermediates of antibiotics, in a simple manner in high yields by utilizing enzymes of microorganisms. The process comprises subjecting 5-(phenyl or substituted phenyl)hydantoins to the action of a cultured broth, cells or treated cells of microorganisms having a capability in asymmetrically hydrolyzing the hydantoin ring, which may be represented by the following equation:

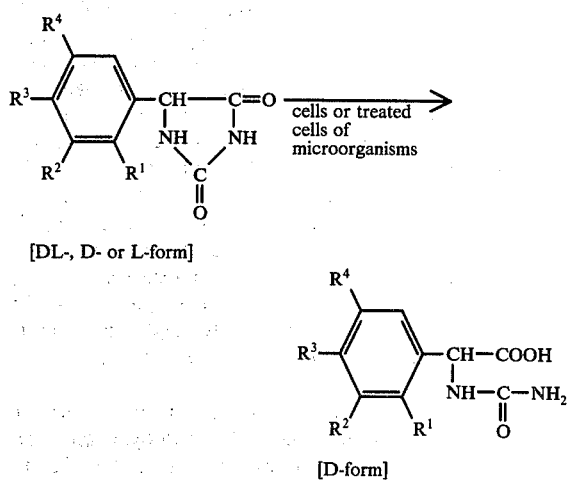

wherein $R^1$, $R^2$, $R^3$ and $R^4$ are independently hydrogen atom, a halogen atom, hydroxyl group, a lower alkoxyl group or methyl group.

DETAILED DESCRIPTION 5-(Phenyl or substituted phenyl)hydantoins employed as the reaction substrate in the present invention are D-, L- and DL-forms thereof. In general, the DL-forms obtained by chemical syntheses are suitably employed. These hydantoins are synthesized from the corresponding benzaldehyde or substituted benzaldehydes by the Bucherer-Berg's method known as a synthetic method of α-amino acids. Some hydantoin compounds may also be synthetically derived from other 5-(substituted phenyl)hydantoins.

The term "5-(phenyl or substituted phenyl)hydantoins" as used herein means 5-phenyl hydantoin and 5-(substituted phenyl)hydantoins, which are represented by the following general formula:

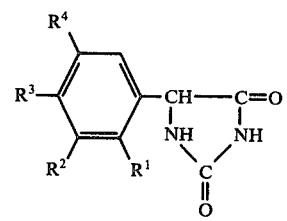

wherein $R^1$, $R^2$, $R^3$ and $R^4$ are independently hydrogen atom, a halogen atom, hydroxyl group, a lower alkoxyl group or methyl group. Typical examples of the 5-(substituted phenyl)hydantoins employed in the present invention are 5-(monosubstituted phenyl)hydantoins such as 5-(2-chlorophenyl)hydantoin, 5-(3-chlorophenyl)hydantoin, 5-(4-chlorophenyl)hydantoin, 5-(2-fluorophenyl)hydantoin, 5-(3-fluorophenyl)hydantoin, 5-(4-fluorophenyl)hydantoin, 5-(2-iodophenyl)hydantoin, 5-(3-iodophenyl)hydantoin, 5-(4-iodophenyl)hydantoin, 5-(2-hydroxyphenyl)hydantoin, 5-(3-hydroxyphenyl)hydantoin, 5-(4-hydroxyphenyl)hydantoin, 5-(2-methoxyphenyl)hydantoin, 5-(3-methoxyphenyl)hydantoin, 5-(4-methoxyphenyl)hydantoin, 5-(2-methylphenyl)hydantoin, 5-(3-methylphenyl)hydantoin and 5-(4-methylphenyl)hydantoin, 5-(disubstituted phenyl) hydantoins such as 5-(2,4-dichlorophenyl)hydantoin, 5-(3,4-dichlorophenyl)hydantoin, 5-(3,5-dichlorophenyl)hydantoin, 5-(2,4-dihydroxyphenyl)hydantoin, 5-(2,5-dihydroxyphenyl)hydantoin, 5-(3,4-dihydroxyphenyl)hydantoin, 5-(2,4-dimethoxyphenyl)hydantoin, 5-(2,5-dimethoxyphenyl)hydantoin, 5-(3,4-dimethoxyphenyl)hydantoin, 5-(3,5-dimethoxyphenyl)hydantoin, 5-(3-chloro-4-hydroxyphenyl)hydantoin, 5-(5-chloro-2-hydroxyphenyl)hydantoin, 5-(3-chloro-4-methoxyphenyl)hydantoin, 5-(2-hydroxy-4-methoxyphenyl)hydantoin, 5-(2-hydroxy-5-methoxyphenyl)hydantoin, 5-(4-hydroxy-3-methoxyphenyl)hydantoin, 5-(4-hydroxy-3-ethoxyphenyl)hydantoin, 5-(4-hydroxy-2-methylphenyl)hydantoin and 5-(4-hydroxy-3-methylphenyl)hydantoin, and 5-(trisubstituted phenyl)hydantoins such as 5-(3,5-dichloro-2-hydroxyphenyl)hydantoin, 5-(3,5-dichloro-4-hydroxyphenyl)hydantoin and 5-(3,5-dimethyl-4-methoxyphenyl)hydantoin.

The microorganisms employed in the present invention are those having a capability in asymmetrically hydrolyzing the hydantoin ring, and such microorganisms are selected by examining the presence of the above capability from wild strains present in nature, strains deposited in public organizations, and microorganisms obtained by artificial mutation from these strains. The expression "capability in asymmetrically hydrolyzing the hydantoin ring" as used herein means a capability to hydrolyze the hydantoin ring of the 5-(phenyl or substituted phenyl)hydantoins so as to substantially produce only D-(−) forms of N-carbamoyl-2-(phenyl or substituted phenyl)glycines. As an examining method of this capability, for instance, a method as stated below may be employed: First, cells are collected by subjecting 2 ml. of a cultured broth of a microorganism to centrifugation, and then washed with 2 ml. of a 0.9% by weight saline water. Again, cells are collected by centrifugation. The thus obtained intact cells (wet weight: 40 to 400 mg.) are added to 2 ml. of a 0.1 to 1.0% by weight aqueous solution or suspension of a substrate. Then, the reaction is carried out at pH 7 to 10 at 30° to 40° C. for 10 to 40 hours. After the completion of the reaction, a concentrated hydrochloric acid solution of p-dimethylaminobenzaldehyde is added to the reaction mixture, and the resulting color-developed reaction mixture is subjected to centrifugation to remove insoluble materials such as cells. Then, the amount of the produced N-carbamoyl-2-(phenyl or substituted phenyl)glycine in the resulting supernatant liquid is determined colorimetrically. With respect to the strain showing the relatively high conversion, the hydrolysis reaction of 5-(phenyl or substituted phenyl)hydantoin is again carried out on a large scale, and the produced N-carbamoyl-2-(phenyl or substituted phenyl)glycine is isolated. Such strains as to be confirmed to produce the D-(−) form of N-carbamoyl-2-(phenyl or substituted phenyl)-glycine are adopted as the microorganisms employed in the present invention.

The microorganisms employed in the present invention are those passing the above examination, being selected from bacteria, actinomycetes, molds, yeasts and deuteromycetes. According to the research of the present inventors, such microorganisms can be found in a very wide range of the genus from the standpoint of taxonomy. For instance, examples of the bacteria are Achromobacter, Aerobacter, Aeromonas, Agrobacterium, Alcaligenes, Arthrobacter, Bacillus, Brevibacterium, Corynebacterium, Enterobacter, Erwinia, Escherichia, Klebsiella, Microbacterium, Micrococcus, Protaminobacter, Proteus, Pseudomonas, Sarcina, Serratia and Xanthomonas. Examples of the actinomycetes are Actinomyces, Actinoplanes, Mycobacterium, Nocardia and Streptomyces. Examples of the molds are Aspergillus, Paecilomyces and Penicillium. Examples of the yeasts are Candida, Rhodotorula, Pichia and Torulopsis.

The process of the present invention utilizes the catalytic action of an intracellular enzyme in the form of the cells or treated cells of microorganisms. The enzyme can be prepared by culturing a microorganism in a conventional manner. Although the culture is usually effected in a liquid medium, solid surface culture may also be employed. In general, carbon and nitrogen sources which microorganisms can assimilate and inorganic salt nutrients essential for the growth of the microorganisms are included in the culture medium. Preferably, a hydantoin compound such as hydantoin, DL-5-methylhydantoin and DL-5-(2-methylthioethyl)-hydantoin is added to the culture medium in an amount of 0.05 to 0.3% by weight to adaptively enhance the desired enzyme activity. The culture conditions are selected from the temperature range of 20° to 85° C. and pH range of 4 to 11 in accordance with the optimum growth conditions of the employed strain, and usually the microorganisms are cultured at a temperature of 20° to 40° C. at a pH of 5 to 9 for 10 to 75 hours. During the culture, the growth of the microorganism may be accelerated by aeration and agitation.

The thus cultured microorganism is employed in a form of the cultured broth, cells or treated cells in the asymmetric hydrolysis reaction of the 5-(phenyl or substituted phenyl)hydantoins. In many cases, the strong reaction can be caused by employing the cultured broth containing the cells of microorganism as it is. However, in cases where the components in the cultured broth are an obstacle to the reaction or it is desired to increase the amount of cells, cells separated from the cultured broth are employed. Although the objects of the invention can be sufficiently attained by employing the intact cells, the cells may be employed in a form of the dried cells, for example, lyophilized cells and acetone powder, for the convenience of the storage or handling. Also, the cells can be employed in a form of the treated cells, for example, crushed cells and cellular extract. Further, these cells and treated cells may be immobilized in a conventional manner.

The reaction substrate is usually admixed with the cultured broth, cells or treated cells in an aqueous medium to make the enzymes of microorganisms act catalytically on the substrate. The hydrolysis reaction may also be effected by adding the reaction substrate to a liquid culture medium during the culture of microorganism. In that case, the growth of microorganism and the hydrolysis reaction proceed in parallel to some extent.

The concentration of the reaction substrate, namely 5-(phenyl or substituted phenyl)hydantoins, is selected from 0.1 to 30% by weight. The solubility of the hydantoin compounds in water is generally low, and in many cases, the hydantoin compounds are present in a suspended form, which is not an obstacle to the reaction since the substrate successively dissolves into the aqueous reaction medium with the progress of the reaction.

When carrying out the hydrolysis reaction of the 5-(phenyl or substituted phenyl)hydantoins in an aqueous reaction medium, the reaction mixture is maintained at a pH of 7 to 10. At this pH range, the desired products can be obtained in high yields as long as microorganisms having high activity are employed. When pH is lower than 7, the reaction rate is very slow. Also, when pH is higher than 10, side reactions may occur. At pH 7 to 10 the conversion rate of the DL-5-(phenyl or substituted phenyl)hydantoins to D-(−)-N-carbamoyl-2-(phenyl or substituted phenyl)glycines is remarkably increased, since the solubility of the substrate increases with increasing pH and the racemization of the hydantoin ring is effectively accelerated under alkaline conditions. With the progress of the reaction the pH of the reaction mixture lowers and, therefore, it is preferable to add at an appropriate time a neutralizing agent such as ammonia, caustic soda, caustic potash and sodium carbonate to the reaction mixture to maintain it at the optimum pH. Also, as occasion demands, an organic solvent and a surface active agent may be added to the reaction medium.

The hydrolysis reaction is carried out at a temperature suitable for the enzyme of the employed microorganism, and usually at a temperature of 20° to 85° C. The reaction time varies depending on the activity of the employed microorganism and the reaction temperature, and is usually selected from 5 to 100 hours, preferably from 5 to 30 hours.

The D-(—)-N-carbamoyl-2-(phenyl or substituted phenyl)glycines produced by the hydrolysis reaction are isolated from the reaction mixture by utilizing pH adjustment or treatment with an ion-exchange resin. For instance, the reaction mixture is adjusted to pH 5 and subjected to centrifugation or filtration to remove insoluble materials such as unchanged substrate and cells, and then the resulting supernatant liquid or filtrate is adjusted to pH 2 to 4 to precipitate the desired product. The N-carbamoyl-2-(hydroxyl-substituted phenyl)glycine compounds among the N-carbamoyl-2-(substituted phenyl)glycines are hardly isolated by the above method, and are isolated by the ion-exchange resin treatment. However, the ion-exchange resin treatment is not limited to such a case, and is available as a general isolating method. After removing insoluble materials from the reaction mixture, the desired product is adsorbed by passing the reaction mixture through a column of a basic anion-exchange resin, and then eluted from the anion-exchange resin with a solvent such as dilute hydrochloric acid. The eluate is then neutralized and concentrated under reduced pressure to recover crystals of the desired product.

D-(—)-N-carbamoyl-2-(phenyl or substituted phenyl)glycines obtained by the process of the present invention are useful intermediates for preparing semi-synthetic penicillins and semi-synthetic cephalosporins, and also can be readily converted to D-(—)-2-(phenyl or substituted phenyl)glycines by hydrolyzing them in an appropriate manner. Therefore, the utility of the present invention is very great. For instance, D-(—)-2-phenylglycine which is the raw material for Ampicillin can be obtained in high yields by reacting D-(—)-N-carbamoyl-2-phenylglycine prepared by the present invention with nitrous acid. In the same manner, D-(—)-2-(4-hydroxyphenyl)glycine which is the raw material for Amoxicillin can be obtained in good yields from D-(—)-N-carbamoyl-2-(4-hydroxyphenyl)glycine. Although it is also known that D-(—)-2-(4-hydroxyphenyl)glycine can be derived from D-(—)-2-(4-methoxyphenyl)glycine, it is also possible to prepare this compound by converting D-(—)-N-carbamoyl-2-(4-methoxyphenyl)glycine obtained according to the present invention.

The present invention is more particularly described and explained by means of the following Examples, in which all percents are percent by weight unless otherwise stated. These examples are intended to illustrate the invention and are not to be construed to limit the scope of the invention.

EXAMPLE 1

A liquid medium of pH 7.0 containing the following components was prepared, and 100 ml. portions thereof were poured into 500 ml. shaking flasks and were steam-sterilized at 120° C. for 10 minutes.

| Medium Components | |
|---|---|
| Meat extract | 0.5 % |
| Yeast extract | 0.5 % |
| Peptone | 1.0 % |
| NaCl | 0.15 % |

To each flask was added 300 mg. of sterilized DL-5-(2-methylthioethyl)hydantoin under sterile conditions. The thus obtained mixtures were employed as culture mediums. Each microorganism shown in Table 1, which was previously cultured on an agar bouillon slant at 33° C. for 24 hours, was inoculated into each culture medium and was cultured at 33° C. for 22 hours with shaking. Cells were separated from the each cultured broth and washed with a 0.9% saline water. The cells were collected again by centrifugation, and then suspended into 33 ml. of a 0.9% saline water. The thus obtained each suspension was employed as a component of the mixture described below.

Mixture Components (1) 33 ml. of aqueous substrate suspension of pH 7.6 containing 1.5% of DL-5-phenylhydantoin (substrate content: 500 mg.)
(2) 33 ml. of 0.2 M phosphate buffer solution of pH 7.6
(3) 33 ml. of cell suspension A 300 ml. ground stopper Erlenmeyer flask was charged with the above components (1), (2) and (3), and then the reaction was carried out at 33° C. for 40 hours with mild shaking. After the completion of the reaction, the reaction mixture was centrifuged and 2 ml. of the obtained supernatant solution was taken out. The supernatant solution was color-developed with 0.5 ml. of a 5% solution of p-dimethylaminobenzaldehyde in 2 N hydrochloric acid, and then the amount of N-carbamoyl-2-phenylglycine was colorimetrically determined by measuring the absorbance at 420 nm. The same procedure as above was repeated by employing each cell suspension. The amounts of the N-carbamoyl-2-phenylglycine produced in the reaction mixtures and the conversions from DL-5-phenylhydantoin are shown in Table 1.

Then, the above supernatant solution was lyophilized, and the obtained powders were dissolved in 5 to 10 ml. of water. After removing the insoluble materials by filtration, the filtrate was adjusted to pH 4 to 3.5 with 2 N hydrochloric acid to give a white precipitate of N-carbamoyl-2-phenylglycine. The precipitate was separated by filtration, and recrystallized from a mixed solvent of water and ethanol to give N-carbamoyl-2-phenylglycine of high purity. The same procedure as above was repeated by employing each supernatant solution.

The infrared spectra and Rf values by silica-gel thin layer chromatography (solvent: n-butanol/acetic acid/water = 4/1/1) of the thus obtained crystals agreed with those of the authentic N-carbamoyl-2-phenylglycine, and also the found data of the elementary analysis agreed with the calculated value. Also, the specific rotatory power of each crystals fell within the range of $[\alpha]_D^{20} = -136.3°$ to $[\alpha]_D^{20} = -133.0°$ and agreed with the value for D-(—)-N-carbamoyl-2-phenylglycine ($[\alpha]_D^{20} = -136.3°$) described in Chemical Abstracts, 65, 3883d(1966).

The reaction products were identified as D-(—)-N-carbamoyl-2-phenylglycine.

Table 1

| Strain | N-carbamoyl-2-phenyl-glycine mg./ml. | Conversion mole % | Amount of obtained N-carbamoyl-2-phenyl-glycine mg. |
|---|---|---|---|
| *Achromobacter delmarvae* IFO 12668 | 0.8 | 15 | 38 |
| *Aerobacter cloacae* IAM 1221 | 2.4 | 44 | 179 |
| *Aeromonas hydrophila* IFO 3820 | 0.06 | 1 | — |
| *Agrobacterium tumefaciens* IFO 3058 | 1.8 | 33 | 127 |
| *Agrobacterium rhizogenes* IFO 13259 | 1.9 | 34 | 129 |
| *Alcaligenes faecalis* IFO 13111 | 0.03 | 0.5 | — |
| *Arthrobacter simplex* IFO 12069 | 0.4 | 7 | 23 |
| *Bacillus sphaericus* IFO 3525 | 0.5 | 9 | 26 |
| *Brevibacterium incertum* IFO 12145 | 1.3 | 24 | 77 |
| *Corynebacterium sepedonicum* IFO 3306 | 2.5 | 45 | 191 |
| *Enterobacter cloacae* IFO 13535 | 0.03 | 0.5 | — |
| *Erwinia aroidiae* IFO 12380 | 0.04 | 0.7 | — |
| *Escherichia coli* ATCC 21148 | 0.03 | 0.5 | — |
| *Klebsiella pneumoniae* IFO 3319 | 0.4 | 7 | 15 |
| *Microbacterium flavum* ATCC 0340 | 1.1 | 20 | 57 |
| *Micrococcus roseus* IFO 3764 | 1.5 | 27 | 89 |
| *Mycobacterium smegmatis* ATCC 607 | 1.7 | 31 | 106 |
| *Nocardia corallina* IFO 3338 | 2.4 | 44 | 155 |
| *Protaminobacter alboflavus* IFO 3707 | 0.5 | 9 | 25 |
| *Proteus morganii* IFO 3848 | 0.5 | 9 | 19 |
| *Pseudomonas aeruginosa* IFO 3445 | 1.5 | 27 | 90 |
| *Pseudomonas chlororaphis* IFO 3904 | 2.0 | 36 | 122 |
| *Pseudomonas desmolytica* IFO 12570 | 1.8 | 33 | 99 |
| *Pseudomonas striata* IFO 12996 | 2.6 | 47 | 222 |
| *Sarcina marginata* IFO 3066 | 0.5 | 9 | 27 |
| *Serratia plymuthicum* IFO 3055 | 0.3 | 5 | 10 |
| *Xanthomonas campestris* IAM 1671 | 0.03 | 0.5 | — |

(Note) The catalogue numbers of strains shown in Table 1 show the strains deposited in the following organizations (hereinafter the same).
IAM: Institute of Applied Microbiology, University of Tokyo, Japan
IFO: Institute for Fermentation, Osaka (Japan)
ATCC: American Type Culture Collection (U.S.A.)

EXAMPLE 2

A liquid medium of pH 7.0 containing the following components was prepared, and 90 ml. portions thereof were poured into 500 ml. shaking flasks and were steam-sterilized at 120° C. for 10 minutes.

| Medium Components | |
|---|---|
| Glucose | 2.0 % |
| Soybean meal | 1.0 % |
| Yeast extract | 0.25 % |
| $(NH_4)_2SO_4$ | 0.1 % |
| $CaCO_3$ | 0.5 % |
| $K_2HPO_4$ | 0.4 % |
| DL-5-(2-methylthioethyl)hydantoin | 0.2 % |

To each flask was added the cultured broth obtained previously by culturing each microorganism shown in Table 2 respectively in 10 ml. of the same liquid medium as above in a test tube at 30° C. for 48 hours, and the culture was carried out at 30° C. for 72 hours with shaking. Cells were separated from each cultured broth by centrifugation, and then cell suspensions were prepared in the same manner as in Example 1.

The hydrolysis reaction of DL-5-phenylhydantoin, the colorimetric determination and the recovery of the produced N-carbamoyl-2-phenylglycine were carried out in the same manner as in Example 1.

The results are shown in Table 2.

Table 2

| Strain | N-carbamoyl-2-phenyl-glycine mg./ml. | Conversion mole % | Amount of obtained N-carbamoyl-2-phenyl-glycine mg. |
|---|---|---|---|
| *Actinomyces griseoruber* IFO 12872 | 0.9 | 16 | 46 |
| *Actinoplanes philippiensis* IAM 0120 | 1.1 | 20 | 47 |
| *Streptomyces almquisti* ATCC 618 | 2.1 | 38 | 151 |
| *Streptomyces aureus* IFO 3175 | 1.2 | 22 | 53 |
| *Streptomyces flaveolus* IFO 3408 | 1.2 | 22 | 55 |
| *Streptomyces griseus* ATCC 10137 | 1.8 | 33 | 122 |

The obtained N-carbamoyl-2-phenylglycine showed the specific rotatory power of $[\alpha]_D^{20} = -136.3°$ to $-133.5°$ (c = 1, 1 N $NH_4OH$), and was identified as D-(−)-N-carbamoyl-2-phenylglycine.

EXAMPLE 3

A liquid medium of pH 7.6 containing the following components was prepared, and 100 ml. portions thereof were poured into 500 ml. shaking flasks and were steam-sterilized at 120° C. for 10 minutes.

| Medium Components | |
|---|---|
| Sucrose | 10.0 % |
| Yeast extract | 0.2 % |
| $(NH_4)_2HPO_4$ | 0.2 % |
| $KH_2PO_4$ | 0.1 % |
| $MgSO_4 \cdot 7H_2O$ | 0.1 % |
| $CaCO_3$ | 0.2 % |
| DL-5-(2-methylthioethyl)hydantoin | 0.2 % |

Each microorganism shown in Table 3, which was previously cultured on a malt agar slant containing 0.3% of DL-5-(2-methylthioethyl)hydantoin at 33° C. for 24 hours, was inoculated into each culture medium, and was cultured at 28° C. for 40 hours with shaking. Cells were separated from the resulting each cultured broth by centrifugation and washed with 50 ml. of a 0.9% saline water. The cells were collected again by centrifugation, and then suspended into 33 ml. of a 0.9% saline water. The thus obtained each cell suspension was employed as a component of the mixture described below.

Mixture Components (1) 33 ml. of aqueous substrate suspension of pH 7.6 containing 3.0% of DL-5-phenylhydantoin (substrate content: 1,000 mg.)
(2) 33 ml. of 0.2 M phosphate buffer solution of pH 7.6
(3) 33 ml. of cell suspension A 300 ml. ground stopper Erlenmeyer flask was charged with the above components (1), (2) and (3), and then the reaction was carried out at 30° C. for 40 hours with mild shaking.

After the completion of the reaction, the colorimetric determination was carried out in the same manner as in Example 1, and it was confirmed that N-carbamoyl-2-phenylglycine was produced in an amount shown in Table 3 in the reaction mixture, respectively.

The reaction mixture was centrifuged and the resulting supernatant solution was passed through a column of a strongly basic anion exchange resin of OH-type to adsorb N-carbamoyl-2-phenylglycine on the resin. Then, N-carbamoyl-2-phenylglycine was eluted with dilute hydrochloric acid, and after neutralization with sodium carbonate the eluate was concentrated under reduced pressure to precipitate the crystals. Recrystallization was conducted.

Infrared spectra, silica-gel thin layer chromatograms and specific rotary powers of the thus obtained crystals indicated that the reaction products were D-(−)-N-carbamoyl-2-phenylglycine.

Table 3

| Strain | N-carbamoyl-2-phenyl-glycine mg./ml. | Conversion mole % | Amount of obtained N-carbamoyl-2-phenyl-glycine mg. |
|---|---|---|---|
| *Candida macedoniensis* IFO 0706 | 0.7 | 6 | 49 |
| *Candida utilis* IAM 4220 | 0.8 | 7 | 65 |
| *Pichia vini* IFO 0795 | 0.5 | 5 | 32 |
| *Rhodotorula glutinis* IFO 0559 | 1.2 | 11 | 89 |
| *Torulopsis utilis* IAM 4246 | 0.05 | 0.5 | — |

EXAMPLE 4

A liquid medium of pH 6.0 containing the following components was prepared, and 90 ml. portions thereof were poured into 500 ml. shaking flasks and were steam-sterilized at 120° C. for 10 minutes.

| Medium Components | |
|---|---|
| Glucose | 10.0 % |
| Peptone | 0.2 % |
| $KNO_3$ | 0.2 % |
| $(NH_4)H_2PO_4$ | 1.0 % |
| $MgSO_4 \cdot 7H_2O$ | 0.05 % |
| $CaCl_2$ | 0.01 % |
| Hydantoin | 0.2 % |

To each flask was added the cultured broth obtained previously by culturing each microorganism shown in Table 4 respectively in 10 ml. of the same liquid medium as above in a test tube at 30° C. for 48 hours, and the culture was carried out at 30° C. for 72 hours with shaking. Cells were separated from the resulting each cultured broth by centrifugation, and then cell suspensions were prepared in the same manner as in Example 1.

The hydrolysis reaction of DL-5-phenylhydantoin and the colorimetric determination of the produced N-carbamoyl-2-phenylglycine were carried out in the same manner as in Example 1.

The results are shown in Table 4.

Table 4

| Strain | N-carbamoyl-2-phenyl-glycine mg./ml. | Conversion mole % |
|---|---|---|
| *Aspergillus nigar* IAM 3009 | 0.06 | 1 |
| *Paecilomyces varioti* IFO 5476 | 0.3 | 5 |
| *Penicillium citrinum* IFO 6352 | 0.05 | 0.5 |

EXAMPLE 5

Cell suspensions of microorganisms shown in Table 5 were prepared in the same manner as in Example 1.

By employing the thus prepared cell suspensions, mixtures having the following composition were prepared, and the hydrolysis reaction was carried out on each mixture in a 300 ml. ground stopper Erlenmeyer flask at 31° C. for 40 hours with mild shaking. During the reaction, the pH of the reaction mixtures was maintained at 9.5 with 2 N KOH.

Mixture Components (1) 500 mg. of DL-5-phenylhydantoin
(2) 67 ml. of 0.1 M $NH_4Cl$—$NH_4OH$ buffer solution of pH 9.5
(3) 33 ml. of cell suspension After the completion of the reaction, the colorimetric determination and recovery of N-carbamoyl-2-phenylglycine were carried out in the same manner as in Example 1.

The results are shown in Table 5.

It is observed that the racemization of the hydantoin ring is accelerated and the conversion is remarkably raised by maintaining the reaction mixture at pH 9.5.

Table 5

| Strain | N-carbamoyl-2-phenyl-glycine mg./ml. | Conversion mole % | Amount of obtained N-carbamoyl-2-phenyl-glycine mg. |
|---|---|---|---|
| Aerobacter cloacae IAM 1221 | 4.4 | 80 | 379 |
| Corynebacterium sepedonicum IFO 3306 | 4.0 | 73 | 318 |
| Pseudomonas striata IFO 12996 | 3.8 | 69 | 303 |
| Control | 0.0 | 0 | — |

The obtained each N-carbamoyl-2-phenylglycine was recrystallized with a mixed solvent of water and ethanol, and the specific rotatory power was measured in the same manner as in Example 1, by which it was confirmed that the reaction products were the D-(—) form.

EXAMPLE 6

Cell suspensions of microorganisms shown in Table 6 were prepared in the same manner as in Example 1. Then, mixtures having the following composition were prepared.

Mixture Components (1) 500 mg. of DL-5-(4-hydroxyphenyl)hydantoin
(2) 67 ml. of 0.1 M $NH_4Cl-NH_4OH$ buffer solution of pH 9.5
(3) 33 ml. of cell suspension The hydrolysis reaction of DL-5-(4-hydroxyphenyl)-hydantoin was carried out in a 300 ml. ground stopper Erlenmeyer flask at 31° C. for 40 hours with mild shaking, respectively. During the reaction, the pH of the reaction mixtures was maintained at 9.5 with 2 N KOH.

After the completion of the reaction, the produced N-carbamoyl-2-(4-hydroxyphenyl)glycine was colorimetrically determined in the same manner as in Example 1. The results are shown in Table 6.

The supernatant solution obtained by centrifuging the reaction mixture was lyophilized, and the residue was extracted with ethanol. After removing insoluble materials by filtration, to the ethanol solution was added ethyl acetate in the weight ratio of ethyl acetate to ethanol of 2:1, and further added about 1.5 equivalents of dicyclohexylamine to give a white precipitate of dicyclohexylamine salt of N-carbamoyl-2-(4-hydroxyphenyl)glycine. The white precipitate was taken out, and was caused to react with 1.1 equivalents of sodium nitrite in an aqueous medium under acidic conditions with hydrochloric acid at room temperature for 1 hour. Then the resulting reaction mixture was passed through a column of a strongly acidic cation exchange resin of H-type (commercially available under the registered trademark "Amberlite IR-120B" made by Rohm & Haas Co.) to adsorb the produced 2-(4-hydroxyphenyl)glycine on the resin. After eluting with 1.5 N $NH_4OH$, crystalline 2-(4-hydroxyphenyl)glycine was isolated by concentrating the eluate under reduced pressure. These procedures were repeated on each reaction mixture.

The infrared spectra and Rf values by silica-gel thin layer chromatography (solvent: n-butanol/acetic acid/water = 4/1/1) of the thus obtained crystals agreed with those of the authentic sample, and also the found data of the elementary analysis agreed with the calculated value. Further, the specific rotatory power of each crystals fell within the range of $[\alpha]_D^{20} = -161.8°$ to $[\alpha]_D^{20} = -158.5°$ (c = 0.5, 1 N HCl) and approximately agreed with the value for D-(—)-2-(4-hydroxyphenyl)glycine, $[\alpha]_D^{24} = -159.1°$ (c = 1, 1 N HCl), described in Japanese Patent Disclosure No. 56946/1974.

It was confirmed that the obtained reaction products were D-(—)-2-(4-hydroxyphenyl)glycine of high purity.

Table 6

| Strain | N-carbamoyl-2-(4-hydroxyphenyl)-glycine mg./ml. | Conversion mole % | Amount of obtained dicyclohexylamine salt of N-carbamoyl-2-(4-hydroxyphenyl)-glycine mg. |
|---|---|---|---|
| Pseudomonas striata IFO 12996 | 4.5 | 82 | 655 |
| Corynebacterium sepedonicum IFO 3306 | 3.0 | 55 | 491 |
| Aerobacter cloacae IAM 1221 | 1.5 | 27 | 249 |
| Agrobacterium rhizogenes IFO 13259 | 0.9 | 16 | 123 |
| Control | 0.0 | 0 | — |

EXAMPLE 7

A liquid culture medium of pH 7.0 containing the following components was prepared, and 90 ml. thereof was placed in a 500 ml. shaking flask and was steam-sterilized at 120° C. for 10 minutes.

| Medium Components | |
|---|---|
| Meat extract | 2.0 % |
| Glycerol | 1.0 % |
| Hydantoin | 0.1 % |

To the flask was added the cultured broth obtained previously by culturing Pseudomonas striata IFO 12996 in 10 ml. of the same liquid medium as above in a test tube at 33° C. for 24 hours, and the culture was carried out at 33° C. for 20 hours with shaking. Cells were separated from the resulting cultured broth by centrifugation and washed with 100 ml. of a 0.9% saline water. The cells were collected again by centrifugation to give 2.62 g. of the intact cells.

The thus obtained intact cells were suspended into 10.4 ml. of a 0.9% saline water, and thereto were added 2.0 g. of acrylamide and 105 mg. of N,N'-methylenebis-(acrylamide) and further added 1.3 ml. of a 5% aqueous solution of dimethylaminopropionitrile and 1.3 ml. of a 2.5% aqueous solution of ammonium persulfate. The resulting mixture was shaken. The mixture gelled after several minutes. The mixture was further maintained at 36° C. for 30 minutes to complete the reaction. To the obtained gel containing cells was added a small amount of a 0.9% saline water, and the gel was crushed in a mortar and the resulting granules were washed with a 0.9% saline water to give 2.5 g. of immobilized cells.

A 200 ml. four neck flask equipped with a stirrer was charged with 2.0 g. of DL-5-(4-hydroxyphenyl)hydantoin and 80 ml. of deionized water. To the flask was added a 2 N aqueous solution of NaOH to adjust the liquid to pH 7.0 and further added the immobilized cells suspended in 110 ml. of deionized water. After adjusting the mixture to pH 8.7, the reaction was carried out at 36° C. with mild agitation. During the reaction, pH of the reaction mixture was maintained at 8.7 with a 2 N aqueous solution of NaOH. The reaction was approximately completed after 15 hours. At that time the total volume of the reaction mixture was 200 ml.

The amount of D-(−)-N-carbamoyl-2-(4-hydroxyphenyl)glycine produced in the reaction mixture was 10.4 mg./ml., and the conversion from DL-5-(4-hydroxyphenyl)hydantoin was 98% by mole.

EXAMPLE 8

The following liquid culture mediums (A) and (B) were prepared, and 100 ml. portions thereof were separately placed in 500 ml. shaking flasks and steam-sterilized at 120° C. for 10 minutes.

| Culture Medium (A) | | Culture Medium (B) | |
| --- | --- | --- | --- |
| Meat extract | 2.0 % | Meat extract | 1.0 % |
| Glycerol | 0.6 % | Peptone | 1.0 % |
| Hydantoin | 0.1 % | Yeast extract | 0.5 % |
| pH | 5.6 | Hydantoin | 0.1 % |
| | | NaCl | 0.15 % |
| | | pH | 7.0 |

Each microorganism shown in Table 7, which was previously cultured on an agar bouillon slant at 30° C. for 24 hours, was inoculated into the culture medium (A) or (B), and was cultured at 30° C. for 20 hours with shaking. Cells were separated from the resulting each cultured broth by centrifugation and washed with 100 ml. of a 0.9% saline water. The cells were collected again by centrifugation, and then suspended into 20 ml. of a 0.9% saline water. The thus obtained each cell suspension was employed as a component of the mixture described below.

Mixture Components (1) 1.6 ml. of aqueous substrate suspension which was prepared by suspending DL-5-(4-methoxyphenyl)hydantoin into a 0.1 M NH$_4$OH—NH$_4$Cl buffer solution and adjusting to pH 9.0 (substrate concentration: 21 mM)

(2) 0.4 ml. of cell suspension

A ground stopper test tube was charged with the above components (1) and (2), and then the reaction was carried out at 30° C. for 20 hours with mild shaking. Immediately after the completion of the reaction, 0.5 ml. of a 10% aqueous solution of trichloroacetic acid, 0.5 ml. of a 10% solution of p-dimethylaminobenzaldehyde in 6 N hydrochloric acid and 3.0 ml. of pure water were added to the reaction mixture and admixed. The resulting color-developed reaction mixture was centrifuged to remove insoluble materials, and N-carbamoyl-2-(4-methoxyphenyl)glycine was colorimetrically determined by measuring the absorbance at 420 nm. These reaction and determination procedures were repeated on each microorganism. The amounts of N-carbamoyl-2-(4-methoxyphenyl)glycine produced in the reaction mixtures and the conversions from DL-5-(4-methoxyphenyl)hydantoin are shown in Table 7.

A large scale reaction using Pseudomonas striata IFO 12996 was further carried out as follows: Into a 0.1 M NH$_4$OH—NH$_4$Cl buffer solution was suspended 1.0 g. of DL-5-(4-methoxyphenyl)hydantoin, and the resulting suspension was adjusted to pH 9.0. Then, 80 ml. of the thus prepared substrate suspension was admixed with 20 ml. of a cell suspension prepared in the same manner as above. After placing the mixture in a 300 ml. ground stopper Erlenmeyer flask, the reaction was carried out at 30° C. for 20 hours with mild shaking. After the completion of the reaction, the reaction mixture was adjusted to pH 5.0 and was centrifuged to remove insoluble materials such as the unaltered substrate and cells. The resulting supernatant solution was adjusted to pH 3.5 to give a white precipitate of N-carbamoyl-2-(4-methoxyphenyl)glycine. The precipitate was separated by filtration and recrystallized from ethanol to give 551 mg. of N-carbamoyl-2-(4-methoxyphenyl)glycine of high purity.

The melting point of the thus obtained N-carbamoyl-2-(4-methoxyphenyl)glycine was 204° C. (decomposition), and the results of the elementary analysis and infrared spectrum were theoretically reasonable. Also, the specific rotatory power was $[\alpha]_D^{24} = -141.8°$ (c = 0.5, 0.1 N NH$_4$OH).

The reaction product was identified as D-(−)-N-carbamoyl-2-(4-methoxyphenyl)glycine.

Table 7

| Strain | Medium | N-carbamoyl-2-(4-methoxyphenyl)-glycine mg./ml. | Conversion mole % |
| --- | --- | --- | --- |
| Aerobacter cloacae IAM 1221 | A | 3.2 | 86 |
| Agrobacterium rhizogenes IFO 13259 | B | 2.1 | 56 |
| Corynebacterium sepedonicum IFO 3306 | B | 2.0 | 53 |
| Microbacterium flavum ATCC 10340 | B | 1.2 | 32 |
| Mycobacterium smegmatis ATCC 607 | B | 1.4 | 37 |
| Nocardia corallina IFO 3338 | B | 2.4 | 65 |
| Pseudomonas chloroaphis IFO 3904 | A | 2.6 | 69 |
| Pseudomonas striata IFO 12996 | A | 2.9 | 78 |

EXAMPLE 9

Cell suspensions of microorganisms shown in Table 8 were prepared in the same manner as in Example 8.

By employing the thus prepared cell suspensions, mixtures having the following composition were prepared, and the hydrolysis reaction of DL-5-(3-hydroxyphenyl)hydantoin was carried out on each mixture in a ground stopper test tube at 30° C. for 40 hours with mild shaking.

Mixture Components (1) 1.6 ml. of aqueous substrate suspension which was prepared by suspending DL-5-(3-hydroxyphenyl)hydantoin into a 0.1 M NH$_4$OH—NH$_4$Cl buffer solution and adjusting to pH 9.0 (substrate concentration: 21 mM)

(2) 0.4 ml. of cell suspension

The colorimetric determination of N-carbamoyl-2-(3-hydroxyphenyl)glycine was made on each reaction mixture in the same manner as in Example 8. The amounts of N-carbamoyl-2-(3-hydroxyphenyl)glycine produced in the reaction mixtures and the conversions from DL-5-(3-hydroxyphenyl)hydantoin are shown in Table 8.

Table 8

| Strain | N-carbamoyl-2-(3-hydroxyphenyl)-glycine mg./ml. | Conversion mole % |
|---|---|---|
| Aerobacter cloacae IAM 1221 | 1.7 | 49 |
| Corynebacterium sepedonicum IFO 3306 | 1.2 | 34 |
| Pseudomonas chlororaphis IFO 3904 | 1.3 | 36 |
| Pseudomonas striata IFO 12996 | 1.9 | 53 |

Further, a large scale reaction using Aerobacter cloacae IAM 1221 was carried out as follows: Into a 0.1 M $NH_4OH$—$NH_4Cl$ buffer solution was suspended 1.0 g. of DL-5-(3-hydroxyphenyl)hydantoin, and the resulting suspension was adjusted to pH 9.0. Then, 80 ml. of the thus prepared substrate suspension was admixed with 20 ml. of a cell suspension prepared in the same manner as in Example 8. After placing the mixture in a 300 ml. ground stopper Erlenmeyer flask, the reaction was carried out at 30° C. for 48 hours with mild shaking. After the completion of the reaction, the reaction mixture was adjusted to pH 4.0 and was centrifuged to remove insoluble materials such as the unaltered substrate and cells. The resulting supernatant solution was lyophilized, and the obtained powders were extracted with methanol. After adding a small amount of silica-gel to the eluate and distilling off methanol, the residue was packed in a column and the desired product was isolated by the following column chromatography. The residue was first developed with acetone, and then the fraction containing N-carbamoyl-2-(3-hydroxyphenyl)glycine was eluted with a mixed solvent of ethanol and methanol. The solvent was distilled away and the obtained powders were recrystallized from a mixture of acetone and water to give 214 mg. of N-carbamoyl-2-(3-hydroxyphenyl)glycine.

The specific rotatory power of the thus obtained N-carbamoyl-2-(3-hydroxyphenyl)glycine was $[\alpha]_D^{24} = -71.7°$ and it was confirmed to be the D-(—) form.

EXAMPLE 10

Cell suspensions of microorganisms shown in Table 9 were prepared in the same manner as in Example 8.

By employing the thus prepared cell suspensions, mixtures having the following composition were prepared, and the hydrolysis reaction of DL-5-(4-chlorophenyl)hydantoin was carried out on each mixture in a ground stopper test tube at 30° C. for 15 hours with mild shaking.

Mixture Components (1) 1.6 ml. of aqueous substrate suspension which was prepared by suspending DL-5-(4-chlorophenyl)-hydantoin into a 0.1 M $NH_4OH$—$NH_4Cl$ buffer solution and adjusting to pH 9.0 (substrate concentration: 21 mM)
(2) 0.4 ml. of cell suspension The colorimetric determination of N-carbamoyl-2-(4-chlorophenyl)glycine was made on each reaction mixture in the same manner as in Example 8. The amounts of N-carbamoyl-2-(4-chlorophenyl)glycine produced in the reaction mixtures and the conversions from DL-5-(4-chlorophenyl)hydantoin are shown in Table 9.

Table 9

| Strain | N-carbamoyl-2-(4-chlorophenyl)-glycine mg./ml. | Conversion mole % |
|---|---|---|
| Aerobacter cloacae IAM 1221 | 2.8 | 73 |
| Corynebacterium sepedonicum IFO 3306 | 0.42 | 11 |
| Pseudomonas chloroaphis IFO 3904 | 3.1 | 81 |
| Pseudomonas striata IFO 12996 | 3.3 | 86 |

Further, a large scale reaction using Pseudomonas chlororaphis IFO 3904 was carried out as follows: Into a 0.1 M $NH_4OH$—$NH_4Cl$ buffer solution was suspended 1.0 g. of DL-5-(4-chlorophenyl)hydantoin, and the resulting suspension was adjusted to pH 9.0. Then, 80 ml. of the thus prepared substrate suspension was admixed with 20 ml. of a cell suspension prepared in the same manner as in Example 8. After placing the mixture in a 300 ml. ground stopper Erlenmeyer flask, the reaction was carried out at 30° C. for 15 hours with mild shaking. After the completion of the reaction, the reaction mixture was adjusted to pH 5.0 and was centrifuged to remove insoluble materials such as the unaltered substrate and cells. The resulting supernatant solution was adjusted to pH 3.5 to give a white precipitate of N-carbamoyl-2-(4-chlorophenyl)glycine. The precipitate was separated by filtration and recrystallized from ethanol to give 656 mg. of N-carbamoyl-2-(4-chlorophenyl)glycine of high purity.

The melting point of the thus obtained N-carbamoyl-2-(4-chlorophenyl)glycine was 191.5° C. (decomposition), and the results of the elementary analysis and infrared spectrum were theoretically reasonable. Also, the specific rotatory power was $[\alpha]_D^{24} = -126.0°$ (c = 0.5, 0.1 N $NH_4OH$).

The reaction product was identified as D-(—)-N-carbamoyl-2-(4-chlorophenyl)glycine.

EXAMPLE 11

The same reaction and determination procedures as in Example 10 were repeated except that DL-5-(3-chlorophenyl)hydantoin was employed instead of DL-5-(4-chlorophenyl)hydantoin and also microorganisms shown in Table 10 were employed.

The amounts of N-carbamoyl-2-(3-chlorophenyl)glycine produced in the reaction mixtures and the conversions from DL-5-(3-chlorophenyl)hydantoin are shown in Table 10.

Table 10

| Strain | N-carbamoyl-2-(3-chlorophenyl)-glycine mg./ml. | Conversion mole % |
|---|---|---|
| Aerobacter cloacae IAM 1221 | 3.0 | 78 |
| Agrobacterium rhizogenes IFO 13259 | 1.3 | 33 |
| Corynebacterium sepedonicum IFO 3306 | 0.28 | 7.4 |
| Microbacterium flavum ATCC 10340 | 0.50 | 13 |
| Nocardia corallina | 1.7 | 45 |

Table 10-continued

| Strain | N-carbamoyl-2-(3-chlorophenyl)-glycine mg./ml. | Conversion mole % |
|---|---|---|
| IFO 3338 | | |
| Pseudomonas chlororaphis IFO 3904 | 2.0 | 52 |
| Pseudomonas striata IFO 12996 | 2.2 | 58 |

Further, the same large scale reaction as in Example 10 was repeated except that DL-5-(3-chlorophenyl)-hydantoin and Agrobacterium rhizogenes IFO 13259 were employed instead of DL-5-(4-chlorophenyl)-hydantoin and Pseudomonas chlororaphis IFO 3904, respectively. From 1.0 g. of DL-5-(3-chlorophenyl)-hydantoin 267 mg. of N-carbamoyl-2-(3-chlorophenyl)glycine was obtained.

The melting point of the thus obtained N-carbamoyl-2-(3-chlorophenyl)glycine was 181° C. (decomposition), and the results of the elementary analysis and infrared spectrum were theoretically reasonable. Also, the specific rotatory power was $[\alpha]_D^{24} = -123.6°$ (c = 0.5, 0.1 N NH$_4$OH).

The reaction product was identified as D-(−)-N-carbamoyl-2-(3-chlorophenyl)glycine.

EXAMPLE 12

Cell suspensions of microorganisms shown in Table 11 were prepared in the same manner as in Example 8.

By employing the thus prepared cell suspensions, mixtures having the following composition were prepared, and the hydrolysis reaction of DL-5-(4-methylphenyl)hydantoin was carried out on each mixture in a ground stopper test tube at 30° C. for 48 hours with mild shaking.

Mixture Components (1) 1.6 ml. of aqueous substrate suspension which was prepared by suspending DL-5-(4-methylphenyl)-hydantoin into a 0.1 M NH$_4$OH—NH$_4$Cl buffer solution and adjusting to pH 9.0 (substrate concentration: 21 mM)

(2) 0.4 ml. of cell suspension

The colorimetric determination of N-carbamoyl-2-(4-methylphenyl)glycine was made on each reaction mixture in the same manner as in Example 8. The amounts of N-carbamoyl-2-(4-methylphenyl)glycine produced in the reaction mixtures and the conversions from DL-5-(4-methylphenyl)hydantoin are shown in Table 11.

Table 11

| Strain | N-carbamoyl-2-(4-methylphenyl)-glycine mg./ml. | Conversion mole % |
|---|---|---|
| Aerobacter cloacae IAM 1221 | 2.2 | 62 |
| Corynebacterium sepedonicum IFO 3306 | 0.23 | 6.5 |
| Pseudomonas chloraphis IFO 3904 | 1.4 | 41 |
| Pseudomonas striata IFO 12996 | 1.7 | 50 |

Further, a large scale reaction using Pseudomonas striata IFO 12996 was carried out as follows: Into a 0.1 M NH$_4$OH—NH$_4$Cl buffer solution was suspended 1.0 g. of DL-5-(4-methylphenyl)hydantoin, and the resulting suspension was adjusted to pH 9.0. Then, 80 ml. of the thus prepared substrate suspension was admixed with 20 ml. of a cell suspension prepared in the same manner as in Example 8, and the mixture was placed in a 300 ml. ground stopper Erlenmeyer flask. The reaction was then carried out at 30° C. for 70 hours with mild shaking. After the completion of the reaction, the reaction mixture was adjusted to pH 5.0 and was centrifuged to remove insoluble materials such as the unaltered substrate and cells. The resulting supernatant solution was then adjusted to pH 3.5 to give a white precipitate of N-carbamoyl-2-(4-methylphenyl)glycine. The precipitate was separated by filtration and recrystallized from ethanol to give 407 mg. of N-carbamoyl-2-(4-methylphenyl)glycine of high purity.

The melting point of the thus obtained N-carbamoyl-2-(4-methylphenyl)glycine was 210° C. (decomposition), and the results of the elementary analysis and infrared spectrum and theoretically reasonable. Also, the specific rotatory power was $[\alpha]_D^{24} = -136.8°$ (c = 0.5, 1 N NH$_4$OH).

The reaction product was identified as D-(−)-N-carbamoyl-2-(4-methylphenyl)glycine.

EXAMPLE 13

Cell suspensions of microorganisms shown in Table 12 were prepared in the same manner as in Example 8.

By employing the thus prepared cell suspensions, mixtures having the following composition were prepared, and the hydrolysis reaction of DL-5-(2,4-dichlorophenyl)hydantoin was carried out on each mixture in a ground stopper test tube at 30° C. for 40 hours with mild shaking.

Mixture Components (1) 1.6 ml. of aqueous substrate suspension which was prepared by suspending DL-5-(2,4-dichlorophenyl)hydantoin into a 0.1 M NH$_4$OH—NH$_4$Cl buffer solution and adjusting to pH 9.0 (substrate concentration: 21 mM)

(2) 0.4 ml. of cell suspension

The colorimetric determination of N-carbamoyl-2-(2,4-dichlorophenyl)glycine was made on each reaction mixture in the same manner as in Example 8. The amounts of N-carbamoyl-2-(2,4-dichlorophenyl)glycine produced in the reaction mixtures and the conversions from DL-5-(2,4-dichlorophenyl)hydantoin are shown in Table 12.

Table 12

| Strain | N-carbamoyl-2-(2,4-dichlorophenyl) glycine mg./ml. | Conversion mole % |
|---|---|---|
| Aerobacter cloacae IAM 1221 | 1.5 | 34 |
| Corynebacterium sepedonicum IFO 3306 | 1.2 | 28 |
| Pseudomonas chlororaphis IFO 3904 | 0.88 | 20 |
| Pseudomonas striata IFO 12996 | 1.6 | 37 |

Further, a large scale reaction using Corynebacterium sepedonicum IFO 3306 was carried out as follows: Into a 0.1 M NH$_4$OH—NH$_4$Cl buffer solution was suspended 1.0 g. of DL-5-(2,4-dichlorophenyl)hydantoin, and the resulting suspension was adjusted to pH 9.0. Then, 80 ml. of the thus prepared substrate suspension was admixed with 20 ml. of a cell suspension prepared in the same manner as in Example 8, and the mixture was placed in a 300 ml. ground stopper Erlenmeyer flask. The reaction was then carried out at 30° C. for 72 hours with mild shaking. After the completion of the reaction, the reaction mixture was adjusted to pH 5.0 and was centrifuged to remove insoluble materials such as the unreacted substrate and cells. The resulting supernatant solution was then adjusted to pH 3.5 to give a white precipitate of N-carbamoyl-2-(2,4-dichlorophenyl)glycine. The precipitate was separated by filtration and recrystallized from ethanol to give 282 mg. of N-carbamoyl-2-(2,4-dichlorophenyl)glycine of high purity.

The melting point of the thus obtained N-carbamoyl-2-(2,4-dichlorophenyl)glycine was 199° C. (decomposition), and the results of the elementary analysis and infrared spectrum were theoretically reasonable. Also, the specific rotatory power was $[\alpha]_D^{24} = -110.2°$ (c = 0.5, 0.1 N $NH_4OH$).

The reaction product was identified as D-(−)-N-carbamoyl-2-(2,4-dichlorophenyl)glycine.

composition of the mixture used in the reaction was shown below.

Mixture Components (1) 1.6 ml. of aqueous substrate suspension which was prepared by suspending a DL-5-(substituted phenyl)hydantoin into a 0.1 M $NH_4OH$—$NH_4Cl$ buffer solution and adjusted to pH 9.0 (substrate concentration: 21 mM)

(2) 0.4 ml. of cell suspension

The mixture of the above components (1) and (2) was placed in a ground stopper test tube, and the hydrolysis reaction was carried out at 30° C. for 40 hours with mild shaking. After the completion of the reaction, the colorimetric determination of the produced N-carbamoyl-2-(substituted phenyl)glycine was made in the same manner as in Example 8.

The amounts of N-carbamoyl-2-(substituted phenyl)glycines produced in the reaction mixtures and the conversions from DL-5-(substituted phenyl)hydantoins are shown in Table 13, respectively.

Table 13

| Reaction product | Streptomyces griseus ATCC 1013 | | Actinoplanes philippiensis IAM 0120 | |
|---|---|---|---|---|
| | Amount mg./ml. | Conversion mole % | Amount mg./ml. | Conversion mole % |
| N-carbamoyl-2-(4-methoxyphenyl)glycine | 1.3 | 34 | 1.0 | 27 |
| N-carbamoyl-2-(3-hydroxyphenyl)glycine | 1.3 | 36 | 0.81 | 23 |
| N-carbamoyl-2-(4-chlorophenyl)glycine | 1.5 | 40 | 2.1 | 54 |
| N-carbamoyl-2-(3-chlorophenyl)glycine | 1.2 | 32 | 1.6 | 42 |
| N-carbamoyl-2-(4-methylphenyl)glycine | 1.2 | 35 | 1.4 | 41 |
| N-carbamoyl-2-(2,4-dichlorophenyl)glycine | 1.5 | 33 | 1.2 | 28 |

EXAMPLE 14

A liquid culture medium of pH 7.0 containing the following components was prepared, and 90 ml. portions thereof were poured into 500 ml. shaking flasks and were steam-sterilized at 120° C. for 10 minutes.

| Medium Components | |
|---|---|
| Glucose | 2.0 % |
| Soybean meal | 1.0 % |
| Yeast extract | 0.25 % |
| Meat extract | 0.1 % |
| $(NH_4)_2SO_4$ | 0.5 % |
| $CaCO_3$ | 0.4 % |
| KCl | 0.4 % |
| $K_2HPO_4$ | 0.02 % |
| DL-5-(2-methylthioethyl)hydantoin | 0.3 % |

As microorganisms, Streptomyces griseus ATCC 10137 and Actinoplanes philippiensis IAM 0120 were employed, and cell suspensions were prepared as follows: To the above shaking flask was added a cultured broth obtained previously by culturing the microorganism in 10 ml. of the same liquid culture medium as above in a test tube at 30° C. for 48 hours with shaking, and the culture was carried out at 30° C. for 48 hours with shaking. Cells were separated from the resulting cultured broth by centrifugation and washed with 100 ml. of a 0.9% saline water. The cells were collected again by centrifugation, and then suspended into 20 ml. of a 0.9% saline water.

By employing the thus prepared cell suspensions, the hydrolysis reactions of DL-5-(4-methoxyphenyl)hydantoin, DL-5-(3-hydroxyphenyl)hydantoin, DL-5-(4-chlorophenyl)hydantoin, DL-5-(3-chlorophenyl)hydantoin, DL-5-(4-methylphenyl)hydantoin and DL-5-(2,4-dichlorophenyl)hydantoin were carried out. The The hydrolysis reaction of DL-5-(4-chlorophenyl)hydantoin was further carried out on a large scale by employing Streptomyces griseus ATCC 10137 as follows: Into a 0.1 M $NH_4OH$—$NH_4Cl$ buffer solution was suspended 1.0 g. of the reaction substrate, and the resulting suspension was adjusted to pH 9.0. Then, 80 ml. of the thus prepared substrate suspension was admixed with 20 ml. of a cell suspension prepared in the same manner as above, and the mixture was placed in a 300 ml. ground stopper Erlenmeyer flask. The reaction was then carried out at 30° C. for 72 hours with mild shaking. After the completion of the reaction, the reaction mixture was treated in the same manner as in Example 10 to give 390 mg. of crystalline N-carbamoyl-2-(4-chlorophenyl)glycine of high purity.

The melting point of the thus obtained crystals was 191° C. (decomposition), and the results of the elementary analysis and infrared spectrum were theoretically reasonable. Also, the specific rotatory power was $[\alpha]_D^{24} = -124.4°$ (c = 0.5, 0.1 N $NH_4OH$).

The reaction product was identified as D-(−)-N-carbamoyl-2-(4-chlorophenyl)glycine.

Also, the hydrolysis reaction of DL-5-(4-methylphenyl)hydantoin was carried out on a large scale by employing Actinoplanes philippiensis IAM 0120 as follows: Into a 0.1 M $NH_4OH$—$NH_4Cl$ buffer solution was suspended 1.0 g. of the reaction substrate, and the resulting suspension was adjusted to pH 9.0. Then, 80 ml. of the thus prepared substrate suspension was admixed with 20 ml. of a cell suspension prepared in the same manner as above, and the mixture was placed in a 300 ml. ground stopper Erlenmeyer flask. The reaction was then carried out at 30° C. for 72 hours with mild shaking. After the completion of the reaction, the reaction mixture was treated in the same manner as in Example 12 to give 295 mg. of crystalline N-carbamoyl-2-(4-methylphenyl)glycine of high purity.

The melting point of the thus obtained crystals was 210° C. (decomposition), and the results of the elementary analysis and infrared spectrum were theoretically reasonable. Also, the specific rotatory power was $[\alpha]_D^{24} = -135.3°$ (c = 0.5, 0.1 N NH$_4$OH).

The reaction product was identified as D-(−)-N-carbamoyl-2-(4-methylphenyl)glycine.

EXAMPLE 15

A liquid medium containing the following components was prepared, and 10 ml. portions thereof were poured into large test tubes.

| Medium Components | |
|---|---|
| Meat extract | 0.5 % |
| Yeast extract | 0.5 % |
| KH$_2$PO$_4$ | 0.2 % |
| MgSO$_4$. 7H$_2$O | 0.1 % |
| CaCl$_2$. 2H$_2$O | 40 p.p.m. |

Then, hydantoin, DL-5-methylhydantoin and DL-5-(2-methylthioethyl)hydantoin were separately added to each test tube, respectively in an amount of 20 mg. (concentration: 0.2%). After adjusting to pH 7.0, each culture medium was steam-sterilized at 120° C. for 15 minutes, and was inoculated with Pseudomonas striata IFO 12996 with a platinum loop. The culture was then carried out at 30° C. for 16 hours with shaking. Cells were separated from the resulting each cultured broth by centrifugation and was washed with 10 ml. of a 0.9% saline water. The cells were collected again by centrifugation, and then suspended into 10 ml. of a 0.9% saline water to give a cell suspension. The same was repeated to give each cell suspension.

Mixtures of (1) 2.0 ml. of an aqueous substrate suspension prepared by suspending DL-5-phenylhydantoin into a 0.1 M NaHCO$_3$—Na$_2$CO$_3$ buffer solution of pH 9.5 (substrate concentration: 1.0%) and (2) 2.0 ml. of the above cell suspension were prepared and placed in test tubes, respectively. The hydrolysis reaction was then carried out at 37° C. for 1 hour with mild shaking. Immediately after the completion of the reaction, 1.0 ml. of a 10% aqueous solution of trichloroacetic acid, 1.0 ml. of a 10% solution of p-dimethylaminobenzaldehyde in 6 N hydrochloric acid and 6.0 ml. of distilled water were added to each reaction mixture and admixed. The resulting each color-developed reaction mixture was centrifuged to remove insoluble materials, and the amounts of N-carbamoyl-2-phenylglycine produced in the reaction mixtures were colorimetrically determined by measuring the absorbance at 420 nm. As a Control, the above procedures were repeated except that no hydantoin compound was employed.

The amounts of N-carbamoyl-2-phenylglycine produced in the reaction mixtures and specific activities of cells are shown in Table 14, respectively. The specific activity of cells was expressed in terms of units per milligram of dried cells and out unit was defined as the activity which converts 1 μ mole of DL-5-phenylhydantoin to N-carbamoyl-2-phenylglycine per minute under the condition described above.

From these results, it was confirmed that the hydantoin compounds added to the culture medium enhanced the asymmetrical hydrolysis capability of the microorganism.

Table 14

| Hydantoin compound | Amount of product mg./ml. | Specific activity of cells unit/mg. of dried cells |
|---|---|---|
| Hydantoin | 2.6 | 0.30 |
| DL-5-methylhydantoin | 2.7 | 0.32 |
| DL-5-(2-methylthioethyl)-hydantoin | 1.3 | 0.20 |
| Control | 1.2 | 0.15 |

What we claim is:

1. A process for preparing D-(−)-N-carbamoyl-2-(phenyl or substituted phenyl)glycines having the following general formula:

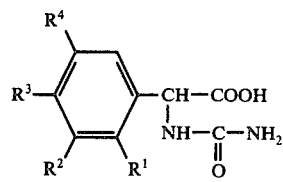

wherein R$^1$, R$^2$, R$^3$ and R$^4$ are independently hydrogen atom, a halogen atom, hydroxyl group, a lower alkoxyl group or methyl group, which comprises subjecting 5-(phenyl or substituted phenyl)hydantoins having the following general formula:

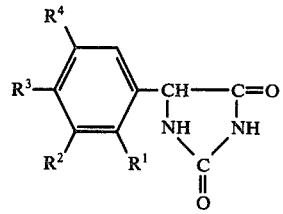

wherein R$^1$, R$^2$, R$^3$ and R$^4$ are as defined above to the action of an enzyme which is in the form of a cultured broth containing microorganisms or the separated cells of said microorganisms in an aqueous medium, said enzyme being capable of hydrolyzing 5-(phenyl or substituted phenyl)hydantoins so as to substantially produce only D-(−)forms of N-carbamoyl-2-(phenyl or substituted phenyl)-glycines, and recovering said D-carbamoyl glycines from the medium.

2. The process of claim 1, wherein said cells are intact cells or dried cells.

3. The process of claim 1, wherein said cells are crushed cells or in the form of a cellular extract.

4. The process of claim 1, wherein said cells are immobilized.

5. The process of claim 1, wherein said microorganisms are those cultured in a culture medium containing a hydantoin compound which enhances the capability of asymmetrically hydrolyzing the hydantoin ring.

6. The process of claim 5, wherein said hydantoin compound is at least one member selected from the group consisting of hydantoin, DL-5-methylhydantoin and DL-5-(2-methylthioethyl)hydantoin.

7. The process of claim 1, wherein said process is conducted in an aqueous medium of pH 7 to 10.

8. The process of claim 7, wherein said microorganism is one member selected from the group consisting of Achromobacter, Aerobacter, Aeromonas, Agrobacterium, Alcaligenes, Arthrobacter, Bacillus, Brevibacterium, Corynebacterium, Enterobacter, Erwinia, Escherichia, Klebsiella, Microbacterium, Micrococcus, Protaminobacter, Proteus, Pseudomonas, Sarcina, Serratia, Xanthomonas, Actinomyces, Actinoplanes, Mycobacterium, Nocardia, Streptomyces, Aspergillus, Paecilomyces, Penicillium, Candida, Pichia, Rhodotorula and Torulopsis.

9. A process for preparing D-(—)-N-carbamoyl-2-phenylglycine which comprises subjecting DL-5-phenylhydantoin to the action of an enzyme which is in the form of a cultured broth containing microorganisms, the separated cells of said microorganisms, the immobilized separated cells of said microoganisms or the immobilized separated cells of said microorganisms that have been cultured in the presence of a hydantoin compound, in an aqueous reaction medium of pH 7 to 10, said enzyme being capable of hydrolyzing 5-(phenyl or substituted phenyl)hydantoins so as to substantially produce only D-(—)forms of N-carbamoyl-2-(phenyl or substituted phenyl)-glycines, and recovering said D-carbamoyl glycines from the medium, said microorganism being one member selected from the group consisting of Aerobacter, Agrobacterium, Brevibacterium, Corynebacterium, Microbacterium, Micrococcus, Pseudomonas, Actinoplanes, Mycobacterium, Nocardia and Streptomyces.

10. A process for preparing D-(—)-N-carbamoyl-2-(hydroxyphenyl)glycine which comprises subjecting DL-5-(hydroxyphenyl)hydantoin to the action of an enzyme which is in the form of a cultured broth containing microorganisms, the separated cells of said microorganisms, the immobilized separated cells of said microorganisms or the immobilized separated cells of said microoganisms that have been cultured in the presence of a hydantoin compound, in an aqueous reaction medium of pH 7 to 10, said enzyme being capable of hydrolyzing 5-(phenyl or substituted phenyl)hydantoins so as to substantially produce only D-(—)forms of N-carbamoyl-2-(phenyl or substituted phenyl)-glycines, and recovering said D-carbamoyl glycines from the medium, said microorganism being one member selected from the group consising of Aerobacter, Agrobacterium, Brevibacterium, Corynebacterium, Microbacterium, Micrococcus, Pseudomonas, Actinoplanes, Mycobacterium, Nocardia and Streptomyces.

11. The process of claim 10, wherein said DL-5-(hydroxyphenyl)hydantoin is DL-5-(4-hydroxyphenyl)-hydantoin.

12. A process for preparing D-(—)-N-carbamoyl-2-(methoxyphenyl)glycine which comprises subjecting DL-5-(methoxyphenyl)hydantoin to the action of an enzyme which is in the form of a cultured broth containing microorganisms, the separated cells of said microorganisms, the immobilized separated cells of said microorganisms or the immobilized separated cells of said microorganisms that have been cultured in the presence of a hydantoin compound, in an aqueous reaction medium of pH 7 to 10, said enzyme being capable of hydrolyzing 5-(phenyl or substituted pheny)hydantoins so as to substantially produce only D-(—)forms of N-carbamoyl-2-(phenyl or substituted phenyl)-glycines, and recovering said D-carbamoyl glycines from the medium, said microorganism being one member selected from the group consisting of Aerobacter, Agrobacterium, Brevibacterium, Corynebacterium, Microbacterium, Micrococcus, Pseudomonas, Actinoplanes, Mycobacterium, Nocardia and Streptomyces.

13. The process of claim 12, wherein said DL-5-(methoxyphenyl)hydantoin is DL-5-(4-methoxyphenyl)-hydantoin.

* * * * *